United States Patent [19]

Ryu

[11] 4,108,920

[45] Aug. 22, 1978

[54] OLIGOMERIZATION OF OLEFINS

[75] Inventor: Ji-Yong Ryu, Des Plaines, Ill.

[73] Assignee: UOP Inc., Des Plaines, Ill.

[21] Appl. No.: 802,334

[22] Filed: Jun. 1, 1977

Related U.S. Application Data

[63] Continuation-in-part of Ser. No. 645,116, Dec. 29, 1975, Pat. No. 4,048,108.

[51] Int. Cl.$^2$ .................................................. C07C 3/10
[52] U.S. Cl. ............................................ 260/683.15 B
[58] Field of Search ................................ 260/683.15 B

[56] References Cited

U.S. PATENT DOCUMENTS 3,153,634   10/1964   Thomas ................................ 252/442

*Primary Examiner*—C. Davis
*Attorney, Agent, or Firm*—James R. Hoatson, Jr.; Raymond H. Nelson; William H. Page, II

[57] ABSTRACT

Olefinic hydrocarbons containing from 3 to about 6 carbon atoms are oligomerized in the presence of a heterogeneous oligomerization catalyst which has been prepared by heating a metal oxide with hydrogen or nitrogen at an elevated temperature, impregnating the heated metal oxide with a solution of titanium tetrafluoride, cold rolling the impregnated oxide followed by steam drying at a temperature of about 100° C. and further drying at an elevated temperature above 100° C.

11 Claims, No Drawings

OLIGOMERIZATION OF OLEFINS

CROSS-REFERENCE TO RELATED APPLICATIONS

This application is a continuation-in-part of my copending application Ser. No. 645,116 filed Dec. 29, 1975, now U.S. Pat. No. 4,048,108, all teachings of which are incorporated herein by reference thereto.

BACKGROUND OF THE INVENTION

Heretofore, the prior art has disclosed catalysts for the polymerization of olefins, said catalysts comprising those known in the art as Ziegler-Natta catalysts. These catalysts typically consist of titanium tetrachloride which has been activated with an aluminum alkyl and operate in the form of a sludge or slurry. For example, U.S. Pat. No. 2,945,845 discloses a titanium tetrachloride catalyst which is used in conjunction with an organic compound such as triethyl aluminum or U.S. Pat. Nos. 3,660,419 and 3,725,497 which also teach the use of titanium tetrachloride catalysts which have been activated with the organoaluminum compounds. Titanium tetrachloride is reduced to lower valent titanium chloride by the aluminum alkyl. Other titanium halide catalysts which have been disclosed in the prior art include those such as shown in U.S. Pat. No. 3,153,634 in which a titanium tetrahalide is impregnated on an alumina such as gamma-alumina and is thereafter subjected to reducing conditions such as by treatment with hydrogen at temperatures ranging from 250° to 500° C. Alternatively, the impregnated alumina could be reduced by contact with a solution or dispersion of a reducing agent such as the alkali or alkaline earth metals or metal hydrides, etc. However, the catalysts thus prepared are useful in polymerizing olefins to form solid polymers, and specifically, high molecular weight solid polymers in which the molecular weight will range from 300 to 100,000. In addition to describing the preparation of solid polymers, this patent also states that aromatic hydrocarbons such as benzene, toluene, xylene or ethers may be used as suitable diluents. However, this is in contradistinction to the heterogeneous oligomerization catalyst of the type hereinafter set forth in greater detail in which it has been found that it is not possible to utilize aromatic hydrocarbons as diluents inasmuch as the olefinic hydrocarbon, if present, would enter into the reaction in which parts or all of the olefin would act as an alkylating agent rather than as a monomer in a polymerization reaction.

Another prior art patent, namely, U.S. Pat. No. 2,965,686, discloses a catalyst which is prepared by activating alumina by evacuation at a temperature of 600° C. for a period ranging from about 18 hours to about 21.5 hours. After activation of the alumina, the base was then treated with a mixture of argon, an inert gas, and titanium tetrachloride vapor at a temperature of about 600° C. for an unspecified period of time. The resultant catalyst was then used in an alkylation reaction for the propylation of cumene to form diisopropylbenzene. This patent is silent as to the type of alumina which was used as the base for the catalyst. In the process of the present invention, as will hereinafter be set forth in greater detail, it is believed that the substrate or base which is utilized must possess surface hydroxyl groups and therefore it is necessary to use specific type of alumina such as gamma-alumina, eta-alumina, etc. Another prior art reference which discloses polymerization catalysts is U.S. Pat. No. 3,506,633 which teaches polymerization catalysts having a chlorine:titanium ratio of 2.5 to 3.5. However, in contradistinction to the catalyst of the present invention, this catalyst is used to prepare solid polymers. Yet another prior patent in this field is U.S. Pat. No. 2,381,481 in which the preparation and use of a catalyst prepared by treating alumina gel with fluotitanic acid is disclosed. However, as is the case of the previously mentioned patents, this catalyst is used to polymerize olefins to heavier hydrocarbons, i.e., solid polymers and is also used to alkylate paraffins with olefins, usually at temperatures ranging between 700° and 900° F. or higher.

It has been known that Lewis acids such as metal halides can catalyze the Friedel-Crafts type reactions and since Lewis acid alone shows no or only mild catalytic activity, Lewis acids normally require cocatalyst. Titanium tetrahalides are well known Lewis acid. (Reference: A. G. Evans, G. W. Meadows and M. Polanyi; Nature (London), 158, 94 (1946)).

As will hereinafter be set forth in greater detail, I have now discovered that olefinic hydrocarbons containing from 3 to about 6 carbon atoms may be oligomerized by treatment with a heterogeneous oligomerization catalyst which is prepared according to the method hereinafter set forth to obtain products which are entirely different than those which were obtained when utilizing the catalysts of the prior art.

This invention relates to a process for the oligomerization of olefinic hydrocarbons. More specifically the invention is concerned with a process for the oligomerization of olefinic hydrocarbons utilizing, as a catalyst system therefor, a catalyst which has been prepared by treating an activated metal oxide which possesses surface hydroxyl groups with a titanium tetrafluoride compound at an elevated temperature.

Many olefinic hydrocarbons which contain from 6 to about 8 carbon atoms in the chain are utilized in various industries in many ways. For example, one specific use of these hydrocarbons, and especially hydrocarbons containing 8 carbon atoms in the chain, is as a component in motor fuels whereby the octane number of the fuel may be improved to a higher level, the presence of these hydrocarbons enabling the motor fuel such as gasoline to possess a relatively high octane number either in the leaded or unleaded state. In addition, another use of hydrocarbons containing the aforementioned number of carbon atoms in the chain would be as starting materials for the preparation of plasticizers.

It is therefore an object of this invention to provide a process for the oligomerization of olefinic hydrocarbons.

A further object of this invention is to provide a process for the oligomerization of olefinic hydrocarbons using a catalyst system which has been prepared in a series of steps hereinafter set forth in greater detail.

In one aspect an embodiment of this invention resides in a process for the oligomerization of an olefin containing from 3 to 6 carbon atoms which comprises oligomerizing said olefin at oligomerization conditions in the presence of a catalyst which has been prepared by heating a metal oxide which possesses surface hydroxyl groups with hydrogen or nitrogen at a temperature of from about 350° C. to about 550° C., impregnating the thus heated metal oxide with a solution of titanium tetrafluoride, cold rolling the impregnated oxide for a period of time ranging from about 0.5 to about 4 hours, then steam drying the composite at a temperature of about 100° C. and further drying the composite at a temperature in the range of from about 200° to about 600° C. in an inert atmosphere, and thereafter recovering the resultant oligomer.

A specific embodiment of this invention is found in a process for the oligomerization of propylene which comprises oligomerizing propylene at a temperature in the range of from about ambient to about 250° C. and a pressure in the range of from about atmospheric to about 100 atmospheres in the presence of a catalyst which has been prepared by heating a low density, high surface area gamma-alumina with nitrogen at a temperature of from about 350° to about 550° C., impregnating the alumina with a solution of titanium tetrafluoride, cold rolling the impregnated oxide for a period of time ranging from about 0.5 to about 4 hours, steam drying the composite at a temperature of about 100° C. and further drying the composite at a temperature in the range of from about 200° to about 600° C. in a nitrogen atmosphere, and recovering the resultant oligomer.

Other objects and embodiments will be found in the following further detailed description of the present invention.

As hereinbefore set forth the present invention is concerned with a process for the oligomerization of olefinic hydrocarbons containing from 3 to about 6 carbon atoms, said oligomerization being effected in the presence of a catalyst of the type hereinafter set forth in greater detail. The term "polymerization" has a relatively broad meaning in the chemical art. Although, it is generally referred to as the preparation of relatively high molecular weight polymers, it may also refer to low molecular weight polymers. In contradistinction to this, the term "oligomerization" refers to polymeric compounds in which the molecule consists of only a relatively few monomer units and would include dimerization, trimerization, or tetramerization. In view of the unpredictable art of catalysis, it was totally unexpected that catalytic compositions of matter which are prepared in a certain manner hereinafter set forth in greater detail would, when used in the treatment of olefinic hydrocarbons, result in the oligomerization of these olefins. This result, that is, the oligomerization of olefinic hydrocarbons, was even unexpected in view of prior art patents containing similar components which, when used in the treatment of olefinic hydrocarbons, resulted in the polymerization of these compounds with the resultant obtention of relatively high molecular weight solid polymers. Therefore, the catalyst of the present invention contrasts with the catalysts of the prior art and due to the different capabilities and functions constitute compounds which possess different characteristics. For example, one catalyst of the prior art was prepared by passing vapor or nitrogen-titanium tetrachloride vapor over a gamma-alumina at a temperature in the range of from about 500° to about 900° C. and thereafter reducing with hydrogen gas at temperatures ranging from 250° to 500° C., the finished catalysts containing from 1 to 10% by weight of titanium trichloride. These catalysts, when used to polymerize olefins, produced solid products possessing molecular weights from 300 to 100,000 when using reaction conditions which included temperatures ranging from 50° to 100° C., pressures ranging from 14.7 to 500 psig and liquid hourly space velocities ranging from 0.1 to 10.

Olefinic hydrocarbons which may undergo oligomerization according to the process of this invention will, as hereinbefore set forth, comprise those olefins containing from 3 to about 6 carbon atoms such as propylene, 1-butene, 2-butene, 1-pentene, 2-pentene, 1-hexene, 2-hexene, 3-hexene, as well as branched chained isomers thereof.

The catalyst system which is used to effect the oligomerization of the aforementioned olefins comprises titanium tetrafluoride impregnated on an activated metal oxide which possesses surface hydroxyl groups. The catalyst which is used in the process of this invention may be prepared by two different techniques. In one method of preparing the catalyst, the sublimation technique is used in which a predetermined amount of solid titanium tetrafluoride is loaded on top of a metal oxide which possesses surface hydroxyl groups. In the preferred embodiment of the invention, the Group IIIA metal oxide will be used, the preferred oxide comprising alumina and particularly a high surface area alumina such as gamma-alumina or, if so desired, eta-alumina or other forms of alumina. The apparent bulk density of the alumina may range from about 0.3 to about 0.7 g/cm$^3$ or higher with a surface area ranging from about 1 to about 500 m$^2$/g. The alumina may be in any shape, one example of the substrate being spheroidal alumina which is prepared by the conventional and commercial oil-drop method as described in U.S. Pat. No. 2,620,314. In addition, it is also contemplated within the scope of this invention that the alumina may be treated to provide greater physical stability, one type of treatment being to impregnate the gamma-alumina with a compound such as barium nitrate which, upon calcination, is converted into barium oxide. The latter compound will then, as hereinbefore set forth, provide greater physical stability for the alumina. It is also contemplated within the scope of this invention that a commercial gamma-alumina may also be used as the support. However, since this commercial gamma-alumina could contain an excessive amount of water which would consume an excess of titanium tetrafluoride without any beneficial effect on the catalyst in the preferred embodiment of this invention, the commercial gamma-alumina is subjected to a predrying step by heating to a temperature in the range of from about 400° to about 600° C. under an inert gas or hydrogen flow for a period of about 1 to about 8 hours. This predrying step is used when preparing a catalyst by the sublimation method or when using an impregnation method using a titanium tetrafluoride solution in organic solvents.

In order to achieve the maximum activity of the metal oxide support, it is necessary to avoid severe drying of said support. For example, the drying of alumina at temperatures in excess of about 600° C., such as 650° C. will seriously deplete the alumina of the hydroxyl groups present thereon. This severe drying step will not only remove the water which is absorbed on the alumina, but will also remove the aforesaid surface hydroxyl groups which are essential to make an active catalyst, said surface hydroxyl groups reacting with the titanium component of the titanium tetrafluoride. The loading of the titanium tetrafluoride on the predried alumina is effected at room temperature under a nitrogen flow. Following the loading, the temperature is then raised to a point higher than the sublimation temperature (284° C.) of the titanium tetrafluoride while maintaining a nitrogen downflow. After the sublimation of the titanium tetrafluoride is accomplished, the temperature is again raised through a series of steps at 350° C. to 400° C. and maintained thereat for a period of time ranging from about 0.5 to about 4 hours.

One disadvantage or drawback when utilizing the sublimation technique is that said technique requires an excess of titanium tetrafluoride in order to insure that all parts of the metal oxide are contacted by the titanium compound. Therefore, in view of this disadvantage, the preferred method of preparing the novel heterogeneous oligomerization catalyst of the present invention will constitute the impregnation technique. When effecting this method, a solution of titanium tetrafluoride in water or an appropriate organic polar solvent in which the titanium tetrafluoride is soluble without the destruction of the titanium tetrafluoride identity is utilized. When utilizing the impregnation technique, a desired amount of titanium tetrafluoride is dissolved in an appropriate solvent in an inert atmosphere which is afforded by the use of an inert gas such as nitrogen, helium, argon, etc. The predried Group IIIA metal oxide support is then impregnated with the solution and cold rolled for a desired period of time followed by a mild steam drying at a temperature of about 100° C. while maintaining an inert atmosphere. Following this, the catalyst is then subjected to further drying at a temperature in the range of from about 200° to about 600° C. while maintaining a downflow of inert gas.

It is also contemplated within the scope of this invention that the impregnation technique may also be effected by utilizing an aqueous titanium tetrafluoride solution. Alternatively, an aqueous solution of titanium hexafluoric acid may be used in place of the aqueous titanium tetrafluoride solution. The impregnation utilizing the aqueous titanium tetrafluoride or aqueous titanium hexafluoric acid can be effected without predrying the metal oxide support. The metal oxide support is impregnated with a solution followed by cold rolling for a period of time which may range from about 0.5 to about 4 hours and thereafter the catalyst composite is dried at a temperature in the range of from about 200° to about 450° C. for a period of time sufficient to decompose the aqueous solution and form the catalyst composite comprising titanium tetrafluoride on the Group IIIA metal oxide support.

Other alternative methods of preparing the heterogeneous oligomerization catalysts of the present invention would be to admix the titanium tetrafluoride in the form of a powder with the metal oxide also in the form of a powder and pelletize the admixture or heat the admixture and use a slurry.

While the aforesaid discussion has been centered upon the use of gamma-alumina as a substrate for the reduced titanium tetrafluoride, it is also contemplated that other Group IIIA metal oxides which possess surface hydroxyl groups and which also possess a relatively high surface area such as gallium oxide, indium oxide and thallium oxide may also be used. However, of these compounds, the preferred substrate is alumina, and especially low density, high surface area aluminas such as gamma-alumina or, if so desired, eta-alumina or other forms of alumina which possess high surface areas.

It is also contemplated within the scope of this invention that the catalyst system hereinbefore described may be composited on a solid support. The preferred solid supports which may be utilized will comprise high surface area inert compounds, some representative examples of these inert solids will include silica or mixtures of silica with other inorganic oxides such as silica-magnesia, silica-zirconia, silica-thoria, silica-magnesia-zirconia, etc.; charcoal, coal, diatomaceous earths and clays, such as fuller's earth, bentonite, montmorillonite, kieselguhr, etc. It is to be understood that these compounds will act only as supports for the catalyst system and will not enter into the catalytic activity of the composite. The titanium tetrafluoride and Group IIIA metal oxide catalyst may be composited on the aforesaid inert supports in any manner known in the art such as by impregnation, deposition, rolling, milling, mixing, etc.

In addition it is also to be considered within the scope of this invention that one or more promoters may be added to the catalyst system. It is believed that use of one or more promoters selected from the metals of Group VIB or Group VIII of the Periodic Table may be beneficial to the practice of the present invention.

The catalysts which are prepared according to the method hereinbefore set forth are utilized to oligomerize olefinic hydrocarbons containing from 3 to about 6 carbon atoms in length and which possess a terminal double bond, the greatest yields of product comprising dimers and trimers of the monomeric olefin. The oligomerization of the olefins is effected in a conventional manner, that is, by placing the titanium tetrafluoride-Group IIIA metal oxide catalyst in an appropriate apparatus which may comprise a reaction flask, autoclave, etc. It is to be understood that the placement of the catalyst in the reaction apparatus is effected while maintaining said catalyst in an inert atmosphere, said atmosphere comprising, as hereinbefore set forth, argon, nitrogen, helium, etc. Thereafter, the olefinic hydrocarbon which is to be oligomerized is charged to the reaction apparatus containing the catalyst at predetermined reaction conditions which may include temperatures ranging from ambient (about 20°–25° C.) to about 250° C. or more, pressures ranging from atmospheric to about 100 atmospheres or more and liquid hourly space velocities ranging from about 0.5 to about 10. It is contemplated within the scope of this invention that the olefins which are to be oligomerized may be admixed with paraffins which will act as diluents for the reaction. However, the olefins may not be admixed with an aromatic diluent unless said aromatic compound is highly alkylated, inasmuch as the aromatic diluent in an unsubstituted form will interfere with the reaction and inhibit the oligomerization of the olefin. Generally, it is not preferred to use aromatic compounds as diluents.

It has been discovered that when utilizing the heterogeneous oligomerization catalysts which are prepared according to the process hereinbefore set forth, the distribution of the reaction products will differ from that which is obtained when utilizing other conventional polymerization catalyst such as Solid Phosphoric Acid. As will hereinafter be shown in greater detail in the examples at the end of the specification, it is possible to obtain a relatively selective reaction product whereby more valuable dimers and trimers of the olefinic hydrocarbon which is undergoing oligomerization will be recovered.

The following examples are given for purposes of illustrating the heterogeneous oligomerization catalysts of the present invention and to the use of these catalysts in oligomerization reactions. However, these examples are given merely for purposes of illustration and are not intended to limit the generally broad scope of the present invention in strict accordance therewith.

EXAMPLE I

A titanium hexafluoric acid solution was prepared by diluting 6.58 grams (4.05 cc) of a 60% titanium hexafluoric acid solution to 350 cc with demineralized water. Following this, 300 cc of gamma-alumina was added to the 350 cc of titanium hexafluoric acid solution and cold rolled for a period of 10 minutes. At the end of this time the composite was steam dried followed by further drying at a temperature of 300° C. for a period of 2.5 hours in a nitrogen atmosphere. The finished catalyst was exposed to air for a period of 12 days following which it was redried at a temperature of 300° C. for a period of 4 hours in a downflow of nitrogen.

The catalyst which was prepared according to the above paragraph was packed in a tubular glass reactor, 30 cc of the catalyst being used for this reaction. Following this, a mixture of propene and helium was passed over the catalyst at a temperature of 200° C. for a period of about 2 hours. The reaction product was recovered and condensed at a temperature of about −78.5° C. and thereafter subjected to chromatographic analysis. The distribution of the product as $C_6$ carbon atom skeletons, given in percent by weight, which was recovered is set forth in the table below.

| | |
|---|---|
| 3,3-Dimethyl-1-butene | 0.3 |
| 4-Methyl-1-pentene } | 2.2 |
| 3-Methyl-1-pentene | |
| 4-Methyl-cis-2-pentene | 1.4 |
| 2,3-Dimethyl-1-butene | 4.4 |
| Unknown | tr |
| 4-Methyl-trans-2-pentene | 5.3 |
| Unknown | 0.7 |
| 1-Hexene } | 9.2 |
| 2-Methyl-1-pentene | |
| 2-Ethyl-1-butene | |
| Trans-3-hexene } | 5.0 |
| Cis-3-hexene | |
| Trans-2-hexene | 4.2 |
| 2-Methyl-2-pentene } | 23.7 |
| Cis-2-hexene | |
| 3-Methyl-cis-2-pentene | 12.5 |
| 3-Methyl-trans-2-pentene | 20.1 |
| Unknown | 0.2 |
| 2,3-Dimethyl-2-butene | 10.8 |

EXAMPLE II

In this example a heterogeneous oligomerization catalyst was prepared in a manner similar to that set forth in Example I above. High surface area gamma-alumina was impregnated with a solution of titanium hexafluoric acid. The drying of the impregnated gamma-alumina was effected at a temperature of 450° C. for a period of 16 hours. The finished catalyst was utilized to oligomerize a propene-helium feed which was effected at a temperature of 250° C. and a rate of 4.06 grams of propene per 100 minutes. The product was recovered at a temperature of about −78.5° C. and subjected to chromatographic analysis. The $C_6$ carbon atom skeleton atom distribution, given in percent by weight, which was recovered is set forth in the table below:

| | |
|---|---|
| 3,3-Dimethyl-1-butene | 0.3 |
| 4-Methyl-1-pentene } | 1.7 |
| 3-Methyl-1-pentene | |
| 4-Methyl-cis-2-pentene | 1.0 |
| 2,3-Dimethyl-1-butene | 3.2 |
| Unknown | 4.1 |
| 4-Methyl-trans-2-pentene | 3.9 |
| Unknown | 13.4 |
| 1-Hexene } | 12.8 |
| 2-Methyl-1-pentene | |
| 2-Ethyl-1-butene | |
| Trans-3-hexene } | 4.3 |
| Cis-3-hexene | |
| Trans-2-hexene | 4.4 |
| 2-Methyl-2-pentene } | 17.6 |
| Cis-2-hexene | |
| 3-Methyl-cis-2-pentene | 8.7 |
| 3-Methyl-trans-2-pentene | 14.2 |
| Unknown | 0.8 |
| 2,3-Dimethyl-2-butene | 9.6 |

EXAMPLE III

In a manner similar to that set forth in the above examples, a different catalyst for the oligomerization of olefinic hydrocarbons was prepared by dissolving 6.34 grams of indium oxide in 500 cc of a nitric acid solution. Following this 100 cc of silica gel granules were added to the solution and the solution was then slowly neutralized with an ammonium hydroxide solution until a pH of 6 was reached. The solution was then steam dried in a rotary dryer and the catalyst base was calcined at 450° C. for 4 hours in air. The heterogeneous oligomerization catalyst was prepared by impregnating 53 cc of the base with 50 cc of a titanium hexafluoric acid which had been prepared by diluting 1 cc of a 60% aqueous titanium hexafluoric acid solution to 50 cc using demineralized water. After impregnation of the base, the product was dried by heating slowly to a temperature of 350° C. and maintaining this temperature for a period of 10 hours while passing a flow of nitrogen gas over the catalyst.

The thus prepared catalyst system was placed in a vertical tubular glass reactor and a mixture of helium and propylene was passed over the reactor in a downflow manner while maintaining the temperature of the reactor at 200° C. The flow rate for the feed stock consisted of 10 cc per minute of helium and 35 cc per minute of propylene. The product was collected at a temperature of −30° C. and subjected to chromatographic analysis after hydrogenation. The major $C_6$–$C_8$ carbon atom skeleton atom distribution consisted of 7.4 wt. % 2,3-dimethylbutane, 24.5 wt. % of 2-methylpentane, 20.3 wt. % 3-methylpentane, 2.5 wt. % of normal hexane, 2.5 wt. % of 2,4-dimethylpentane, 2.84 wt. % of 2-methyl hexane, 6.3 wt. % of 2,3-dimethylpentane, 3.3 wt. % of 3-methylhexane, the remainder being various other isomers.

EXAMPLE IV

In this example 250 cc of 1/16 inch spherical gamma-alumina which had previously been dried at a temperature of 550° C. for a period of 3 hours in a nitrogen flow of 1500 cc/min. was mixed with anhydrous titanium tetrafluoride powder in a nitrogen atmosphere. The admixture was then loaded in a vertical silica tube and subjected to heat treatment in a nitrogen flow of 1500 cc/min. at a temperature of 350° C. for a period of 2.25 hours followed by a treatment at 500° C. for an additional period of 1 hour. The changed catalyst was found to contain 2.78% titanium and 3.55% fluorine by weight.

The catalyst prepared according to the above paragraph in an amount of 50 cc was packed in a tubular glass reactor and propylene was passed over the catalyst at a flow rate of 108 cc/min. at a temperature of 215° C. and atmospheric pressure. The reaction product was recovered and condensed at a temperature of about −30° C. After a period of 220 minutes, 11.1 grams of reaction product was recovered. The product was then subjected to chromatographic analysis, the distribution of product by weight % as the carbon number is set forth in the following table:

| Carbon No. | Weight |
|---|---|
| $C_{8-}$ | 63.0 |
| $C_9$ | 12.9 |
| $C_{10}$ | 9.1 |
| $C_{11}$ | 5.5 |
| $C_{12}$ | 4.1 |
| $C_{13}$ | 2.1 |
| $C_{14}$ | 1.7 |
| $C_{15}$ | 1.5 |
| $C_{16+}$ | 0.1 |

EXAMPLE V

In a manner similar to that set forth in Example IV above, 200 cc of 1/16 inch spherical gamma-alumina which possessed an apparent bulk density of about 0.5 was predried at a temperature of 550° C. for a period of 3 hours under a nitrogen flow of 2000 cc/min. The alumina was then impregnated in a steam rotary dryer with a titanium tetrafluoride solution in absolute ethyl alcohol under a nitrogen atmosphere. The titanium tetrafluoride solution which was used to impregnate the alumina was prepared by dissolving anhydrous titanium tetrafluoride powder in 500 ml of absolute ethyl alcohol in a nitrogen atmosphere. Following impregnation of the alumina with the titanium tetrafluoride solution, the impregnated alumina spheres were cold rolled for 10 minutes and thereafter steam dried at 100° C. The impregnation product after steam drying was further dried in a vertical silica tube under a nitrogen flow of 1500 cc/min. The drying was effected at a temperature of 140° C. for a period of 1 hour, 200° C. for 1.5 hours, 250° C. for 1 hour, 300° C. for 0.25 hours, and 450° C. for 3 hours.

The catalyst which was thus prepared was packed in a tubular glass reactor using 48 cc of the catalyst. As in Example IV, propylene was charged to the reactor and passed over the catalyst at a flow rate of 105 cc/min. utilizing reaction conditions which included a temperature of 215° C. and atmospheric pressure. After a period of 226 minutes, 10.1 grams of reaction product was recovered by condensation at a temperature of −30° C. The product was subjected to chromatographic analysis and the distribution of the product by weight % according to the carbon number is set forth in the following table.

| Carbon No. | Weight % |
|---|---|
| $C_{8-}$ | 56.4 |
| $C_9$ | 16.7 |
| $C_{10}$ | 9.3 |
| $C_{11}$ | 5.7 |
| $C_{12}$ | 5.1 |
| $C_{13}$ | 2.8 |
| $C_{14}$ | 2.4 |
| $C_{15}$ | 1.5 |
| $C_{16+}$ | 0.1 |

I claim as my invention:

1. A process for the oligomerization of an olefin containing from 3 to 6 carbon atoms which comprises oligomerizing said olefin at oligomerization conditions in the presence of a catalyst which has been prepared by heating a metal oxide which possesses surface hydroxyl groups with hydrogen or nitrogen at a temperature of from about 350° C. to about 550° C., impregnating the thus heated metal oxide with a solution of titanium tetrafluoride, cold rolling the impregnated oxide for a period of time ranging from about 0.5 to about 4 hours, then steam drying the composite at a temperature of about 100° C. and further drying the composite at a temperature in the range of from about 200° to about 600° C. in an inert atmosphere, and thereafter recovering the resultant oligomer.

2. The process as set forth in claim 1 in which said oligomerization conditions include a temperature of from about ambient to about 250° C. and a pressure from about atmospheric to about 100 atmospheres.

3. The process as set forth in claim 1 in which said olefin is propylene.

4. The process as set forth in claim 1 in which said olefin is butene-1 or butene-2.

5. The process as set forth in claim 1 in which said metal oxide which possesses surface hydroxyl groups is an oxide of a metal of Group IIIA of the Periodic Table.

6. The process as set forth in claim 5 in which said metal oxide is a low density, high surface area gamma-alumina.

7. The process as set forth in claim 5 in which said metal oxide is gallium oxide.

8. The process as set forth in claim 5 in which said metal oxide is indium oxide.

9. The process as set forth in claim 1 in which said solution of titanium tetrafluoride is an aqueous solution of titanium hexafluoric acid.

10. The process as set forth in claim 1 in which said catalyst is composited on a high surface area solid support.

11. The process as set forth in claim 10 in which said high surface area solid support is silica.

* * * * *